United States Patent [19]
Chee et al.

[11] Patent Number: 5,856,104
[45] Date of Patent: Jan. 5, 1999

[54] POLYMORPHISMS IN THE GLUCOSE-6 PHOSPHATE DEHYDROGENASE LOCUS

[75] Inventors: Mark Chee; Jian-Bing Fan, both of Palo Alto, Calif.

[73] Assignee: Affymetrix, Inc., Santa Clara, Calif.

[21] Appl. No.: 813,508

[22] Filed: Mar. 7, 1997

Related U.S. Application Data

[60] Provisional application No. 60/029,374, Oct. 28, 1996.

[51] Int. Cl.$^6$ .............................. C12Q 1/68; C07H 21/04
[52] U.S. Cl. ........................... 435/6; 435/91.1; 435/91.2; 536/23.5; 536/24.31; 536/24.33
[58] Field of Search .............................. 435/6, 91.1, 91.2, 435/183; 536/23.5, 24.31, 24.33; 935/1, 8, 11, 76, 77

[56] References Cited

U.S. PATENT DOCUMENTS

| | | | |
|---|---|---|---|
| 5,206,137 | 4/1993 | Ip et al. ....................................... | 435/6 |
| 5,292,639 | 3/1994 | Beitz et al. .................................. | 435/6 |
| 5,468,610 | 11/1995 | Polymeropoulos et al. ................ | 435/6 |

OTHER PUBLICATIONS

Nierman and Maglott, eds., ATCC/NIH Repository Catalogue of Human and Mouse DNA Probes and Libraries, Eighth edition, pp. 1–70., 1989.

Sigma Molecular Biology catalog, p. 54., 1989.

Chen et al., "Long–range sequence analysis in uman chromosome Xq28: thirteen known and six candidate genes in 219.4 kb of high GC DNA between the RCP/GCP and G6PD loci," Hum. Mol. Genet. vol. 5, no. 5, pp. 659–668; sequence comparison with Table 2 and, 1996.

Cappellini, Maria Domenica et al., "Multiple G6PD Mutations Are Associated With a Clinical and Biochemical Phenotype Similar to That of G6PD Mediterranean", *Blood,* vol. 87, (May 1, 1996) No. 9, pp. 3953–3958.

Fan, Jian–Bing et al., "Screening the Human Genome for Single–nucleotide Polymorphisms by Hybridization to High–density Oligonucleotide Arrays", Mutation Detection '97, 4th International Workshop, (May 29–Jun. 2, 1997) 1 page.

Kwok, Pui–Yan et al., "Increasing the Information Content of STS–Based Genome Maps: Identifying Polymorphisms in Mapped STSs", *Genomics,* (1996) vol. 31, Article No. 0019, pp. 123–126.

*Primary Examiner*—Bradley L. Sisson
*Attorney, Agent, or Firm*—Townsend & Townsend & Crew

[57] ABSTRACT

The invention provides nucleic acid segments of the glucose-6 phosphate dehydrogenase locus of the human genome including polymorphic sites. Allele-specific primers and probes hybridizing to regions flanking these sites are also provided. The nucleic acids, primers and probes are used in applications such as forensics, paternity testing, medicine and genetic analysis.

13 Claims, No Drawings

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

TGAGCAACAG TGGAAATTTG 20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

TGAGCAACAA TGGAAATTTG 20

( 2 ) INFORMATION FOR SEQ ID NO:3:

( i ) SEQUENCE CHARACTERISTICS:
        ( A ) LENGTH: 20 base pairs
        ( B ) TYPE: nucleic acid ( C ) STRANDEDNESS: single
        ( D ) TOPOLOGY: linear ( i i ) MOLECULE TYPE: DNA ( x i ) SEQUENCE DESCRIPTION: SEQ ID NO:3:

GCAGTTTGAG TGTCTCTGGT 20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GCAGTTTGAA TGTCTCTGGT 20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

GTAAATGCTC TGCAAATAAC 20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

GTNANTNCTG NGCAANTANC 20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

GGCTCCAAGC GGTGCCCGGC 20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

GGCTCCAAGC GGTGCNCGNC                    20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

GGCTCCAAGC GGTGNNCGNC                    20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

GGCTCCAAGC GGTGCNNGNC                    20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

GGCTCCAAGC GGTGCCCGNC                    20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

GGCTCCAAGC GGTGCNNGGN                    20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

GGCTCNNNNT NGNNNNNNNC                    20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

GGCTCCAAGC GGTGCNCGGC 20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

GGCTCCNAAT GGTNNNNGNC 20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

GACCTCTTTA GCTCGTTATT 20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

GACCTCTTTT GCTCGTTATT 20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

GGGCCTCAAG ATTTGATTTC 20

( 2 ) INFORMATION FOR SEQ ID NO:19:

( i ) SEQUENCE CHARACTERISTICS:
        ( A ) LENGTH: 20 base pairs
        ( B ) TYPE: nucleic acid (C) STRANDEDNESS: single
        (D) TOPOLOGY: linear (ii) MOLECULE TYPE: DNA (xi) SEQUENCE DESCRIPTION: SEQ ID NO:19:

GGGCCTCANT ATTTGATTTC 20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

AGGGGGGCTT TTTCCAGCTC 20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

AGGGGGGCTC TTTCCAGCTC 20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

GCCTCCTTCG TTCTACGACA 20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

GCCTCCTTNA TTCTACGACA 20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA ( x i ) SEQUENCE DESCRIPTION: SEQ ID NO:24:

GCCTCCTTCA TTCTACGACA 20

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

AGGGTGCGCG TCCTCACCTG 20

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

AGNGTNCGNA TCCTCACCTG 20

( 2 ) INFORMATION FOR SEQ ID NO:27:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

NGGGTGCGCG TCCTCANCTG 20

( 2 ) INFORMATION FOR SEQ ID NO:28:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

AACCAGAATT TATTTTGAGG 20

( 2 ) INFORMATION FOR SEQ ID NO:29:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

AACCAGAATG TATTTTGAGG 20

POLYMORPHISMS IN THE GLUCOSE-6 PHOSPHATE DEHYDROGENASE LOCUS

CROSS-REFERENCE TO RELATED APPLICATION

The present application claims priority from provisional application 60/029,374, filed Oct. 28, 1996, which is incorporated by reference in its entirety for all purposes.

BACKGROUND OF THE INVENTION

The genomes of all organisms undergo spontaneous mutation in the course of their continuing evolution generating variant forms of progenitor sequences (Gusella, *Ann. Rev. Biochem.* 55, 831–854 (1986)). The variant form may confer an evolutionary advantage or disadvantage relative to a progenitor form or may be neutral. In some instances, a variant form confers a lethal disadvantage and is not transmitted to subsequent generations of the organism. In other instances, a variant form confers an evolutionary advantage to the species and is eventually incorporated into the DNA of many or most members of the species and effectively becomes the progenitor form. In many instances, both progenitor and variant form(s) survive and co-exist in a species population. The coexistence of multiple forms of a sequence gives rise to polymorphisms.

Several different types of polymorphism have been reported. A restriction fragment length polymorphism (RFLP) means a variation in DNA sequence that alters the length of a restriction fragment as described in Botstein et al., *Am. J. Hum. Genet.* 32, 314–331 (1980). The restriction fragment length polymorphism may create or delete a restriction site, thus changing the length of the restriction fragment. RFLPs have been widely used in human and animal genetic analyses (see WO 90/13668; WO90/11369; Donis-Keller, *Cell* 51, 319–337 (1987); Lander et al., *Genetics* 121, 85–99 (1989)). When a heritable trait can be linked to a particular RFLP, the presence of the RFLP in an individual can be used to predict the likelihood that the animal will also exhibit the trait.

Other polymorphisms take the form of short tandem repeats (STRs) that include tandem di-, tri- and tetranucleotide repeated motifs. These tandem repeats are also referred to as variable number tandem repeat (VNTR) polymorphisms. VNTRs have been used in identity and paternity analysis (U.S. Pat. No. 5,075,217; Armour et al., *FEBS Lett.* 307, 113–115 (1992); Horn et al., WO 91/14003; Jeffreys, EP 370,719), and in a large number of genetic mapping studies.

Other polymorphisms take the form of single nucleotide variations between individuals of the same species. Such polymorphisms are far more frequent than RFLPS, STRs and VNTRs. Some single nucleotide polymorphisms occur in protein-coding sequences, in which case, one of the polymorphic forms may give rise to the expression of a defective or other variant protein and, potentially, a genetic disease. Examples of genes, in which polymorphisms within coding sequences give rise to genetic disease include β-globin (sickle cell anemia) and CFTR (cystic fibrosis). Other single nucleotide polymorphisms occur in noncoding regions. Some of these polymorphisms may also result in defective protein expression (e.g., as a result of defective splicing). Other single nucleotide polymorphisms have no phenotypic effects.

Single nucleotide polymorphisms can be used in the same manner as RFLPs, and VNTRs but offer several advantages. Single nucleotide polymorphisms occur with greater frequency and are spaced more uniformly throughout the genome than other forms of polymorphism. The greater frequency and uniformity of single nucleotide polymorphisms means that there is a greater probability that such a polymorphism will be found in close proximity to a genetic locus of interest than would be the case for other polymorphisms. Also, the different forms of characterized single nucleotide polymorphisms are often easier to distinguish that other types of polymorphism (e.g., by use of assays employing allele-specific hybridization probes or primers).

Despite the increased amount of nucleotide sequence data being generated in recent years, only a minute proportion of the total repository of polymorphisms in humans and other organisms has so far been identified. The paucity of polymorphisms hitherto identified is due to the large amount of work required for their detection by conventional methods. For example, a conventional approach to identifying polymorphisms might be to sequence the same stretch of oligonucleotides in a population of individuals by didoxy sequencing. In this type of approach, the amount of work increases in proportion to both the length of sequence and the number of individuals in a population and becomes impractical for large stretches of DNA or large numbers of persons.

SUMMARY OF THE INVENTION

The invention provides nucleic acid segments of between 10 and 100 bases containing at least 10, 15 or 20 contiguous amino acids from any of the sequences shown in any of TABLE 2 (SEQ ID NOS:1 and 2), TABLE 3 (SEQ ID NOS:3 and 4), TABLE 4 (SEQ ID NOS:5 and 6), TABLE 5 (SEQ ID NOS:7–15), TABLE 6 (SEQ ID NOS:16 and 17), TABLE 7 (SEQ ID NOS:18 and 19), TABLE 8 (SEQ ID NOS:20 and 21), TABLE 9 (SEQ ID NOS:22–24), TABLE 10 (SEQ ID NOS:25–27) and TABLE 11 (SEQ ID NOS:28 and 29) including a polymorphic site. Complements of these segments are also included. The segments can be DNA or RNA, and can be double- or single-stranded. Some segments are 10–20 or 10–50 bases long. Preferred segments include a diallelic polymorphic 25 site.

The invention further provides allele-specific oligonucleotides that hybridizes to a sequence shown in TABLE 2 (SEQ ID NOS:1and 2), TABLE 3(SEQ ID NOS:3 and 4), TABLE 4 (SEQ ID NOS:5 and 6), TABLE 5 (SEQ ID NOS:7–15), TABLE 6 (SEQ ID NOS:16 and 17), TABLE 7 (SEQ ID NOS:18 and 19), TABLE 8 (SEQ ID NOS:20 and 21), TABLE 9 (SEQ ID NOS:22–24), TABLE 10 (SEQ ID NOS:25–27) and TABLE 11 (SEQ ID NOS:28 and 29) or its complement. These oligonucleotides can be probes or primers.

The invention further provides a method of analyzing a nucleic acid from an individual. The method determines which base is present at any one of the polymorphic sites shown in TABLE 2(SEQ ID NOS:1 and 2), TABLE 3 (SEQ ID NOS:3 and 4), TABLE 4 (SEQ ID NOS:5 and 6), TABLE 5 (SEQ ID NOS:7–15), TABLE 6 (SEQ ID NOS:16 and 17), TABLE 7 (SEQ ID NOS:18 and 19), TABLE 8 (SEQ ID NOS:20 and 21), TABLE 9 (SEQ ID NOS:22–24), TABLE 10 (SEQ ID NOS:25–27) and TABLE 11 (SEQ ID NOS:28 and 29). Optionally, a set of bases occupying a set of the polymorphic sites shown in TABLE 2 (SEQ ID NOS:1 and 2), TABLE 3 (SEQ ID NOS:3 and 4), TABLE 4 (SEQ ID NOS:5 and 6), TABLE 5 (SEQ ID NOS:7–15), TABLE 6 (SEQ ID NOS:16 and 17), TABLE 7 (SEQ ID NOS:18 and 19), TABLE 8 (SEQ ID NOS:20 and 21), TABLE 9 (SEQ ID NOS:22–24), TABLE 10 (SEQ ID NOS:25–27) and TABLE 11 (SEQ ID NOS:28 and 29). is determined. This type of analysis can be performed on a plurality of individuals who are tested for the presence of a disease phenotype. The presence or absence of disease phenotype can then be correlated with a base or set of bases present at the polymorphic sites in the individuals tested.

DEFINITIONS

An oligonucleotide can be DNA or RNA, and single- or double-stranded. Oligonucleotides can be naturally occurring or synthetic, but are typically prepared by synthetic means. Preferred oligonucleotides of the invention include segments of DNA, or their complements including any one of the polymorphic sites shown in TABLE 2 (SEQ ID NOS:1 and 2), TABLE 3 (SEQ ID NOS:3 and 4), TABLE 4 (SEQ ID NOS:5 and 6), TABLE 5 (SEQ ID NOS:7–15), TABLE 6 (SEQ ID NOS:16 and 17), TABLE 7 (SEQ ID NOS:18 and 19), TABLE 8 (SEQ ID NOS:20 and 21), TABLE 9 (SEQ ID NOS:22–24), TABLE 10 (SEQ ID NOS:25–27) and TABLE 11 (SEQ ID NOS:28 and 29). The segments are usually between 5 and 100 bases, and often between 5–10, 5–20, 10–20, 10–50, 20–50 or 20–100 bases. The polymorphic site can occur within any position of the segment. The segments can be from any of the allelic forms of DNA shown in TABLE2 (SEQ ID NOS:1 and 2), TABLE 3 (SEQ ID NOS:3 and 4), TABLE 4 (SEQ ID NOS:5 and 6), TABLE 5 (SEQ ID NOS:7–15), TABLE 6 (SEQ ID NOS:16 and 17), TABLE 7 (SEQ ID NOS:18 and 19), TABLE 8 (SEQ ID NOS:20 and 21), TABLE 9 (SEQ ID NOS:22–24), TABLE 10 (SEQ ID NOS:25–27) and TABLE 11 (SEQ ID NOS:28 and 29).

Hybridization probes are oligonucleotides capable of binding in a base-specific manner to a complementary strand of nucleic acid. Such probes include peptide nucleic acids, as described in Nielsen et al., *Science* 254, 1497–1500 (1991).

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

Linkage describes the tendency of genes, alleles, loci or genetic markers to be inherited together as a result of their location on the same chromosome, and can be measured by percent recombination between the two genes, alleles, loci or genetic markers.

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as a the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A single nucleotide polymorphism occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

Hybridizations are usually performed under stringent conditions, for example, at a salt concentration of no more than 1M and a temperature of at least 25° C. For example, conditions of 5X SSPE (750 mM NaCl, 50 mM NaPhosphate, 5 mM EDTA, pH 7.4) and a temperature of 25°–30° C. are suitable for allele-specific probe hybridizations.

An isolated nucleic acid means an object species invention) that is the predominant species present (i.e., on a molar basis it is more abundant than any other individual species in the composition). Preferably, an isolated nucleic acid comprises at least about 50, 80 or 90 percent (on a molar basis) of all macromolecular species present. Most preferably, the object species is purified to essential homogeneity (contaminant species cannot be detected in the composition by conventional detection methods).

DESCRIPTION OF THE PRESENT INVENTION

I. Novel Polymorphisms of the Invention

The human glucose-6-phosphate dehyrogenase locus (G6PD) encompasses more than 50,000 bp and resides on the X chromosome. A complete prototypical sequence of the G6PD locus has been published. That locus has remained relatively unexplored due to the cost and difficulty of conventional sequence analysis. The published sequence shows that the G6PD locus contains at least two genes, the G6PD gene and the 2_19 gene. Those genes span approximately 16,000 bp and 10,000 bp, respectively. The enzyme G6PD play a fundamental role in glucose metabolism. The function of the 2–19 polypeptide product, however, has not been shown.

The present application provides 10 polymorphisms at 10 sequence tagged sites in the human G6PD locus. Table 1 shows the base occupied at those ten sites in 10 individuals. The sequences flanking each of these polymorphisms are shown in TABLE 2 (SEQ ID NOS:1 and 2), TABLE 3 (SEQ ID NOS:3 and 4), TABLE 4 (SEQ ID NOS:5 and 6), TABLE 5 (SEQ ID NOS:7–15), TABLE 6 (SEQ ID NOS:16 and 17), TABLE 7 (SEQ ID NOS:18 and 19), TABLE 8 (SEQ ID NOS:20 and 21), TABLE 9 (SEQ ID NOS:22–24), TABLE 10 (SEQ ID NOS:25–27) and TABLE 11 (SEQ ID NOS:28 and 29). The polymorphic site is flanked by bold lines in the table. The sequences designated M1–M10 represent novel allelic variants of this site. The designation N as it appears in Tables 1–11 means the identity of a base was not determined.

II. Analysis of Polymorphisms

A. Preparation of Samples

Polymorphisms are detected in a target nucleic acid from an individual being analyzed. For assay of genomic DNA, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed.

Many of the methods described below require amplification of DNA from target samples. This can be accomplished by e.g., PCR. See generally *PCR Technology: Principles and Applications for DNA Amplification* (ed. H. A. Erlich, Freeman Press, N.Y., N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (eds. McPherson et al., IRL Press, Oxford); and U.S. Pat. No. 4,683,202 (each of which is incorporated by reference for all purposes).

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA,* 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

B. Detection of Polymorphisms in Target DNA

There are two distinct types of analysis depending whether a polymorphism in question has already been characterized. The first type of analysis is sometimes referred to as de novo characterization. This analysis compares target sequences in different individuals to identify points of variation, i.e., polymorphic sites. By analyzing a groups of individuals representing the greatest ethnic diversity among humans and greatest breed and species variety in plants and animals, patterns characteristic of the most common alleles/haplotypes of the locus can be identified, and the frequencies of such populations in the population determined. Additional allelic frequencies can be determined for subpopulations characterized by criteria such as geography, race, or gender. The de novo identification of the polymorphisms of the invention is described in the Examples section. The second type of analysis is determining which form(s) of a characterized polymorphism are present in individuals under test. There are a variety of suitable procedures, which are discussed in turn.

1. Allele-Specific Probes

The design and use of allele-specific probes for analyzing polymorphisms is described by e.g., Saiki et al., *Nature* 324, 163–166 (1986); Dattagupta, EP 235,726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15 mer at the 7 position; in a 16 mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

2. Tiling Arrays

The polymorphisms can also be identified by hybridization to nucleic acid arrays, some example of which are described by WO 95/11995 (incorporated by reference in its entirety for all purposes). One form of such arrays is described in the Examples section in connection with de novo identification of polymorphisms. The same array or a different array can be used for analysis of characterized polymorphisms. WO 95/11995 also describes subarrays that are optimized for detection of a variant forms of a precharacterized polymorphism. Such a subarray contains probes designed to be complementary to a second reference sequence, which is an allelic variant of the first reference sequence. The second group of probes is designed by the same principles as described in the Examples except that the probes exhibit complementarily to the second reference sequence. The inclusion of a second group (or further groups) can be particular useful for analyzing short subsequences of the primary reference sequence in which multiple mutations are expected to occur within a short distance commensurate with the length of the probes (i.e., two or more mutations within 9 to 21 bases).

3. Allele-Specific Primers

An allele-specific primer hybridizes to a site on target DNA overlapping a polymorphism and only primes amplification of an allelic form to which the primer exhibits perfect complementarily. See Gibbs, *Nucleic Acid Res.* 17, 2427–2448 (1989). This primer is used in conjunction with a second primer which hybridizes at a distal site. Amplification proceeds from the two primers leading to a detectable product signifying the particular allelic form is present. A control is usually performed with a second pair of primers, one of which shows a single base mismatch at the polymorphic site and the other of which exhibits perfect complementarily to a distal site. The single-base mismatch prevents amplification and no detectable product is formed. The method works best when the mismatch is included in the 3'-most position of the oligonucleotide aligned with the polymorphism because this position is most destabilizing to elongation from the primer. See, e.g., WO 93/22456.

4. Direct-Sequencing

The direct analysis of the sequence of polymorphisms of the present invention can be accomplished using either the dideoxy chain termination method or the Maxam Gilbert method (see Sambrook et al., *Molecular Cloning, A Laboratory Manual* (2nd Ed., CSHP, New York 1989); Zyskind et al., *Recombinant DNA Laboratory Manual*, (Acad. Press, 1988)).

5. Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., *PCR Technology, Principles and Applications for DNA Amplification*, (W.H. Freeman and Co, New York, 1992), Chapter 7.

6. Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., *Proc. Nat. Acad. Sci.* 86, 2766–2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target sequences.

III. Methods of Use

After determining polymorphic form(s) present in an individual at one or more polymorphic sites, this information can be used in a number of methods.

A. Forensics

Determination of which polymorphic forms occupy a set of polymorphic sites in an individual identifies a set of polymorphic forms that distinguishes the individual. See generally National Research Council, *The Evaluation of Forensic DNA Evidence* (Eds. Pollard et al., National Academy Press, DC, 1996). Since the polymorphic sites are within a 50,000 bp region in the human genome, the probability of recombination between these polymorphic sites is low. That low probability means the haplotype (the set of all 10 polymorphic sites) set forth in this application should be inherited without change for at least several generations. The more sites that are analyzed the lower the probability that the set of polymorphic forms in one individual is the same as that in an unrelated individual. Preferably, if multiple sites are analyzed, the sites are unlinked. Thus, polymorphisms of the invention are often used in conjunction with polymorphisms in distal genes. Preferred polymorphisms for use in forensics are diallelic because the population frequencies of two polymorphic forms can usually be determined with greater accuracy than those of multiple polymorphic forms at multi-allelic loci.

The capacity to identify a distinguishing or unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance.

p(ID) is the probability that two random individuals have the same polymorphic or allelic form at a given polymorphic site. In diallelic loci, four genotypes are possible: AA, AB, BA, and BB. If alleles A and B occur in a haploid genome of the organism with frequencies x and y, the probability of each genotype in a diploid organism are (see WO 95/12607):

$$Homozygote: p(AA)=x^2$$

$$Homozygote: p(BB)=y^2=(1-x)^2$$

$$Single\ Heterozygote: p(AB)=p(BA)=xy=x(1-x)$$

$$Both\ Heterozygotes: p(AB+BA)=2xy=2x(1-x)$$

The probability of identity at one locus (i.e, the probability that two individuals, picked at random from a population will have identical polymorphic forms at a given locus) is given by the equation:

$$p(ID)=(x^2)^2+(2xy)^2+(y^2)^2.$$

These calculations can be extended for any number of polymorphic forms at a given locus. For example, the probability of identity p(ID) for a 3-allele system where the alleles have the frequencies in the population of x, y and z, respectively, is equal to the sum of the squares of the genotype frequencies:

$$p(ID)=x^4+(2xy)^2+(2yz)^2+(2xz)^2+z^4+y^4$$

In a locus of n alleles, the appropriate binomial expansion is used to calculate p(ID) and p(exc).

The cumulative probability of identity (cum p(ID)) for each of multiple unlinked loci is determined by multiplying the probabilities provided by each locus.

$$cum\ p(ID)=p(ID1)p(ID2)p(ID3)\ldots p(IDn)$$

The cumulative probability of non-identity for n loci (i.e. the probability that two random individuals will be different at 1 or more loci) is given by the equation:

$$cum\ p(nonID)=1-cum\ p(ID).$$

If several polymorphic loci are tested, the cumulative probability of non-identity for random individuals becomes very high (e.g., one billion to one). Such probabilities can be taken into account together with other evidence in determining the guilt or innocence of the suspect.

B. Paternity Testing

The object of paternity testing is usually to determine whether a male is the father of a child. In most cases, the mother of the child is known and thus, the mother's contribution to the child's genotype can be traced. Paternity testing investigates whether the part of the child's genotype not attributable to the mother is consistent with that of the putative father. Paternity testing can be performed by analyzing sets of polymorphisms in the putative father and the child.

If the set of polymorphisms in the child attributable to the father does not match the putative father, it can be concluded, barring experimental error, that the putative father is not the real father. If the set of polymorphisms in the child attributable to the father does match the set of polymorphisms of the putative father, a statistical calculation can be performed to determine the probability of coincidental match.

The probability of parentage exclusion (representing the probability that a random male will have a polymorphic form at a given polymorphic site that makes him incompatible as the father) is given by the equation (see WO 95/12607):

$$p(exc)=xy(1-xy)$$

where x and y are the population frequencies of alleles A and B of a diallelic polymorphic site.

(At a triallelic site p(exc)=xy(1−xy)+yz(1−yz)+xz(1−xz)+3xyz(1−xyz))), where x, y and z and the respective population frequencies of alleles A, B and C).

The probability of non-exclusion is $$p(non-exc)=1-p(exc)$$

The cumulative probability of non-exclusion (representing the value obtained when n loci are used) is thus:

$$cum\ p(non-exc)=p(non-exc1)p(non-exc2)p(non-exc3)\ldots p(non-excn)$$

The cumulative probability of exclusion for n loci (representing the probability that a random male will be excluded)

$$cum\ p(exc)=1-cum\ p(non-exc).$$

If several polymorphic loci are included in the analysis, the cumulative probability of exclusion of a random male is very high. This probability can be taken into account in assessing the liability of a putative father whose polymorphic marker set matches the child's polymorphic marker set attributable to his/her father.

C. Correlation of Polymorphisms with Phenotypic Traits

The polymorphisms of the invention may contribute to the phenotype of an organism in different ways. Some polymorphisms occur within a protein coding sequence and contribute to phenotype by affecting protein structure. The effect may be neutral, beneficial or detrimental, or both beneficial and detrimental, depending on the circumstances. For example, a heterozygous sickle cell mutation confers resistance to malaria, but a homozygous sickle cell mutation is usually lethal. Other polymorphisms occur in noncoding regions but may exert phenotypic effects indirectly via influence on replication, transcription, and translation. A single polymorphism may affect more than one phenotypic trait. Likewise, a single phenotypic trait may be affected by polymorphisms in different genes. Further, some polymorphisms predispose an individual to a distinct mutation that is causally related to a certain phenotype.

Phenotypic traits include diseases that have known but hitherto unmapped genetic components. Phenotypic traits also include symptoms of, or susceptibility to, multifactorial diseases of which a component is or may be genetic, such as autoimmune diseases, inflammation, cancer, diseases of the nervous system, and infection by pathogenic microorganisms. Some examples of autoimmune diseases include rheumatoid arthritis, multiple sclerosis, diabetes (insulin-dependent and non-independent), systemic lupus erythematosus and Graves disease. Some examples of cancers include cancers of the bladder, brain, breast, colon, esophagus, kidney, leukemia, liver, lung, oral cavity, ovary, pancreas, prostate, skin, stomach and uterus. Phenotypic traits also include characteristics such as longevity, appearance (e.g., baldness, obesity), strength, speed, endurance, fertility, and susceptibility or receptivity to particular drugs or therapeutic treatments.

Correlation is performed for a population of individuals who have been tested for the presence or absence of a phenotypic trait of interest and for polymorphic markers sets. To perform such analysis, the presence or absence of a set of polymorphisms (i.e. a polymorphic set) is determined for a set of the individuals, some of whom exhibit a particular trait, and some of which exhibit lack of the trait. The alleles of each polymorphism of the set are then reviewed to determine whether the presence or absence of a particular allele is associated with the trait of interest. Correlation can be performed by standard statistical methods such as a κ-squared test and statistically significant correlations between polymorphic form(s) and phenotypic characteristics are noted. For example, it might be found that the presence of allele A1 at polymorphism A correlates with heart disease. As a further example, it might be found that the combined presence of allele A1 at polymorphism A and allele B1 at polymorphism B correlates with increased milk production of a farm animal.

Such correlations can be exploited in several ways. In the case of a strong correlation between a set of one or more polymorphic forms and a disease for which treatment is available, detection of the polymorphic form set in a human or animal patient may justify immediate administration of treatment, or at least the institution of regular monitoring of the patient. Detection of a polymorphic form correlated with serious disease in a couple contemplating a family may also be valuable to the couple in their reproductive decisions. For example, the female partner might elect to undergo in vitro fertilization to avoid the possibility of transmitting such a polymorphism from her husband to her offspring. In the case of a weaker, but still statistically significant correlation between a polymorphic set and human disease, immediate therapeutic intervention or monitoring may not be justified. Nevertheless, the patient can be motivated to begin simple life-style changes (e.g., diet, exercise) that can be accomplished at little cost to the patient but confer potential benefits in reducing the risk of conditions to which the patient may have increased susceptibility by virtue of variant alleles. Identification of a polymorphic set in a patient correlated with enhanced receptiveness to one of several treatment regimes for a disease indicates that this treatment regime should be followed.

For animals and plants, correlations between characteristics and phenotype are useful for breeding for desired characteristics. For example, Beitz et al., U.S. Pat. No. 5,292,639 discuss use of bovine mitochondrial polymorphisms in a breeding program to improve milk production in cows. To evaluate the effect of mtDNA D-loop sequence polymorphism on milk production, each cow was assigned a value of 1 if variant or 0 if wildtype with respect to a prototypical mitochondrial DNA sequence at each of 17 locations considered. Each production trait was analyzed individually with the following animal model:

$$Y_{ijkpn}=\mu+YS_i+P_j+X_k+\beta_1+\ldots\beta_{17}+PE_n+a_n+e_p$$

where $Y_{ijknp}$ is the milk, fat, fat percentage, SNF, SNF percentage, energy concentration, or lactation energy record; $\mu$ is an overall mean; $YS_i$ is the effect common to all cows calving in year-season; $X_k$ is the effect common to cows in either the high or average selection line; $\beta_1$ to $\beta_{17}$ are the binomial regressions of production record on mtDNA D-loop sequence polymorphisms; $PE_n$ is permanent environmental effect common to all records of cow n; $a_n$ is effect of animal n and is composed of the additive genetic contribution of sire and dam breeding values and a Mendelian sampling effect; and $e_p$ is a random residual. It was found that eleven of seventeen polymorphisms tested influenced at least one production trait. Bovines having the best polymorphic forms for milk production at these eleven loci are used as parents for breeding the next generation of the herd.

D. Genetic Mapping of Phenotypic Traits

The previous section concerns identifying correlations between phenotypic traits and polymorphisms that directly or indirectly contribute to those traits. The present section describes identification of a physical linkage between a genetic locus associated with a trait of interest and polymorphic markers that are not associated with the trait, but are in physical proximity with the genetic locus responsible for the trait and co-segregate with it. Such analysis is useful for mapping a genetic locus associated with a phenotypic trait to a chromosomal position, and thereby cloning gene(s) responsible for the trait. See Lander et al., *Proc. Natl. Acad. Sci.* (USA) 83, 7353–7357 (1986); Lander et al., *Proc. Natl. Acad. Sci.* (USA) 84, 2363–2367 (1987); Donis-Keller et al., *Cell* 51, 319–337 (1987); Lander et al., *Genetics* 121, 185–199 (1989)). Genes localized by linkage can be cloned by a process known as directional cloning. See Wainwright, *Med. J. Australia* 159, 170–174 (1993); Collins, *Nature Genetics* 1, 3–6 (1992) (each of which is incorporated by reference in its entirety for all purposes).

Linkage studies are typically performed on members of a family. Available members of the family are characterized for the presence or absence of a phenotypic trait and for a set of polymorphic markers. The distribution of polymorphic markers in an informative meiosis is then analyzed to determine which polymorphic markers co-segregate with a phenotypic trait. See, e.g., Kerem et al., *Science* 245, 1073–1080 (1989); Monaco et al., *Nature* 316, 842 (1985); Yamoka et al., *Neurology* 40, 222–226 (1990); Rossiter et al., *FASEB Journal* 5, 21–27 (1991).

Linkage is analyzed by calculation of LOD (log of the odds) values. A lod value is the relative likelihood of obtaining observed segregation data for a marker and a genetic locus when the two are located at a recombination fraction θ, versus the situation in which the two are not linked, and thus segregating independently (Thompson & Thompson, *Genetics in Medicine* (5th ed, W.B. Saunders Company, Philadelphia, 1991); Strachan, "Mapping the human genome" in *The Human Genome* (BIOS Scientific Publishers Ltd, Oxford), Chapter 4). A series of likelihood ratios are calculated at various recombination fractions (θ), ranging from θ=0.0 (coincident loci) to θ=0.50 (unlinked). Thus, the likelihood at a given value of θ is: probability of data if loci linked at θ to probability of data if loci unlinked. The computed likelihoods are usually expressed as the $\log_{10}$ of this ratio (i.e., a lod score). For example, a lod score of 3 indicates 1000:1 odds against an apparent observed linkage being a coincidence. The use of logarithms allows data collected from different families to be combined by simple addition. Computer programs are available for the calculation of lod scores for differing values of θ (e.g., LIPED, MLINK (Lathrop, *Proc. Nat. Acad. Sci.* (USA) 81, 3443–3446 (1984)). For any particular lod score, a recombination fraction may be determined from mathematical tables. See Smith et al., *Mathematical tables for research workers in human genetics* (Churchill, London, 1961); Smith, *Ann. Hum. Genet.* 32, 127–150 (1968). The value of θ at which the lod score is the highest is considered to be the best estimate of the recombination fraction.

Positive lod score values suggest that the two loci are linked, whereas negative values suggest that linkage is less likely (at that value of θ) than the possibility that the two loci are unlinked. By convention, a combined lod score of +3 or greater (equivalent to greater than 1000:1 odds in favor of linkage) is considered definitive evidence that two loci are linked. Similarly, by convention, a negative lod score of −2 or less is taken as definitive evidence against linkage of the two loci being compared. Negative linkage data are useful in excluding a chromosome or a segment thereof from consideration. The search focuses on the remaining non-excluded chromosomal locations.

IV. Modified Polypeptides and Gene Sequences

The invention further provides variant forms of nucleic acids and corresponding proteins. The nucleic acids comprise at least ten contiguous bases of one of the sequences described in TABLE 2 (SEQ ID NOS:1 and 2), TABLE 3 (SEQ ID NOS:3 and 4), TABLE 4 (SEQ ID NOS:5 and 6), TABLE 5 (SEQ ID NOS:7–15), TABLE 6 (SEQ ID NOS:16 and 17), TABLE 7 (SEQ ID NOS:18 and 19), TABLE 8 (SEQ ID NOS:20 and 21), TABLE 9 (SEQ ID NOS:22–24), TABLE 10 (SEQ ID NOS:25–27) and TABLE 11 (SEQ ID NOS:28 and 29). designated M1–M10. Some nucleic acid encode full-length variant forms of proteins. Similarly, variant proteins have the prototypical amino acid sequences of encoded by nucleic acid sequence shown in Tables 2–11, designated M1–M10 (read so as to be in-frame with the full-length coding sequence of which it is a component).

Variant genes can be expressed in an expression vector in which a variant gene is operably linked to a native or other promoter. Usually, the promoter is a eukaryotic promoter for expression in a mammalian cell. The transcription regulation sequences typically include a heterologous promoter and optionally an enhancer which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the variant gene, both prokaryotic and eukaryotic. Suitable host cells include bacteria such as *E. coli*, yeast, filamentous fungi, insect cells, mammalian cells, typically immortalized, e.g., mouse, CHO, human and monkey cell lines and derivatives thereof. Preferred host cells are able to process the variant gene product to produce an appropriate mature polypeptide. Processing includes glycosylation, ubiquitination, disulfide bond formation, general post-translational modification, and the like.

The protein may be isolated by conventional means of protein biochemistry and purification to obtain a substantially pure product, i.e., 80, 95 or 99% free of cell component contaminants, as described in Jacoby, *Methods in Enzymology* Volume 104, Academic Press, New York (1984); Scopes, *Protein Purification, Principles and Practice,* 2nd Edition, Springer-Verlag, New York (1987); and Deutscher (ed), *Guide to Protein Purification, Methods in Enzymology*, Vol. 182 (1990). If the protein is secreted, it can be isolated from the supernatant in which the host cell is grown. If not secreted, the protein can be isolated from a lysate of the host cells.

The invention further provides transgenic nonhuman animals capable of expressing an exogenous variant gene and/or having one or both alleles of an endogenous variant gene inactivated. Expression of an exogenous variant gene is usually achieved by operably linking the gene to a promoter and optionally an enhancer, and microinjecting the construct into a zygote. See Hogan et al., "Manipulating the Mouse Embryo, A Laboratory Manual," Cold Spring Harbor Laboratory. Inactivation of endogenous variant genes can be achieved by forming a transgene in which a cloned variant gene is inactivated by insertion of a positive selection marker. See Capecchi, *Science* 244, 1288–1292 (1989). The transgene is then introduced into an embryonic stem cell, where it undergoes homologous recombination with an endogenous variant gene. Mice and other rodents are preferred animals. Such animals provide useful drug screening systems.

In addition to substantially full-length polypeptides expressed by variant genes, the present invention includes biologically active fragments of the polypeptides, or analogs thereof, including organic molecules which simulate the interactions of the peptides. Biologically active fragments include any portion of the full-length polypeptide which confers a biological function on the variant gene product, including ligand binding, and antibody binding. Ligand binding includes binding by nucleic acids, proteins or polypeptides, small biologically active molecules, or large cellular structures.

Polyclonal and/or monoclonal antibodies that specifically bind to variant gene products but not to corresponding prototypical gene products are also provided. Antibodies can be made by injecting mice or other animals with the variant gene product or synthetic peptide fragments thereof. Monoclonal antibodies are screened as are described, for example, in Harlow & Lane, *Antibodies, A Laboratory Manual*, Cold Spring Harbor Press, New York (1988); Goding, *Monoclonal antibodies, Principles and Practice* (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

V. Kits

The invention further provides kits comprising at least one allele-specific oligonucleotide as described above. Often, the kits contain one or more pairs of allele-specific oligonucleotides hybridizing to different forms of a polymorphism. In some kits, the allele-specific oligonucleotides are provided immobilized to a substrate. For example, the same substrate can comprise allele-specific oligonucleotide probes for detecting at least 10, 100 or all of the polymorphisms shown in Tables 2–11. Optional additional components of the kit include, for example, restriction enzymes, reverse-transcriptase or polymerase, the substrate nucleoside triphosphates, means used to label (for example, an avidinenzyme conjugate and enzyme substrate and chromogen if the label is biotin), and the appropriate buffers for reverse transcription, PCR, or hybridization reactions. Usually, the kit also contains instructions for carrying out the methods.

EXAMPLES

The polymorphisms set forth in this application were identified by hybridization to tiling arrays. Tiling arrays are described in PCT/US94/12305 (incorporated by reference in its entirety for all purposes). Tiling generally means the synthesis of a defined set of oligonucleotide probes that is made up of a sequence complementary to the sequence to be analyzed (the "target sequence"), as well as preselected variations of that sequence. The variations usually include substitution at one or more base positions with one or more nucleotides. Tiling strategies are discussed in WO 95/11995 (incorporated by reference in its entirety for all purposes). With a tiled array containing 4L probes one can query every position in a nucleotide containing L number of bases. A 4L tiled array, for example, contains L number of sets of 4 probes, i.e. 4L probes. Each set of 4 probes contains the perfect complement to a portion of the target sequence with a single substitution for each nucleotide at the same position in the probe. See also Chee, M., et. al., Science, October, 1996.

To detect the novel sequence tagged polymorphic sites provided in this application, we designed a $P^{25,13}$ (25-mer probes having the interrogation position at base 13) 4L tiling array for the G6PD locus. Because the G6PD locus contains a large number of Alu sequences (repeat sequences), we simplified the tiled probe array by not probing the repetitive Alu sequences. To generate target sequence fragments, blood was collected from 10 individuals. Long range PCR amplification was carried out on genomic DNA. The amplicons were labeled, fragmented, and used to determine hybridization to the array.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

TABLE 1

|     | 1 | 2 | 3 | 4 | 5 | 6 | 7 | 8 | 9 | 10 |
|-----|---|---|---|---|---|---|---|---|---|----|
| M1  | G | G | C | T | C | T | G | C | G | G  |
| M2  | A | A | C | T | C | A | T | C | G | G  |
| M3  | A | A | C | T | C | A | T | C | G | G  |
| M4  | A | A | C | G | C | A | G | C | G | A  |
| M5  | G | G | G | T | C | A | G | C | G | G  |
| M6  | A | A | C | T | T | A | G | C | A | G  |
| M7  | G | G | C | T | C | A | G | C | G | G  |
| M8  | G | G | C | T | C | A | G | C | G | G  |
| M9  | A | A | C | T | T | A | G | C | A | G  |
| M10 | G | G | C | T | C | A | G | T | G | G  |

TABLE 2

| | | | | | | | | | | | | | | | | | | SEQ ID NO: |
|---|---|---|---|---|---|---|---|---|---|---|---|---|---|---|---|---|---|---|
| starting sequence | T | G | A | G | C | A | A | C | A | G | T | G | G | A | A | A | T | T | T | G | 1 |
| M1 | T | G | A | G | C | A | A | C | A | G | T | G | G | A | A | A | T | T | T | G | 1 |
| M10 | T | G | A | G | C | A | A | C | A | G | T | G | G | A | A | A | T | T | T | G | 1 |
| M2 | T | G | A | G | C | A | A | C | A | A | T | G | G | A | A | A | T | T | T | G | 2 |
| M3 | T | G | A | G | C | A | A | C | A | A | T | G | G | A | A | A | T | T | T | G | 2 |
| M4 | T | G | A | G | C | A | A | C | A | A | T | G | G | A | A | A | T | T | T | G | 2 |
| M5 | T | G | A | G | C | A | A | C | A | G | T | G | G | A | A | A | T | T | T | G | 1 |
| M6 | T | G | A | G | C | A | A | C | A | A | T | G | G | A | A | A | T | T | T | G | 2 |
| M7 | T | G | A | G | C | A | A | C | A | G | T | G | G | A | A | A | T | T | T | G | 1 |
| M8 | T | G | A | G | C | A | A | C | A | G | T | G | G | A | A | A | T | T | T | G | 1 |
| M9 | T | G | A | G | C | A | A | C | A | A | T | G | G | A | A | A | T | T | T | G | 2 |

TABLE 3

| | | | | | | | | | | | | | | | | | | SEQ ID NO: |
|---|---|---|---|---|---|---|---|---|---|---|---|---|---|---|---|---|---|---|
| starting sequence | G | C | A | G | T | T | T | G | A | G | T | G | T | C | T | C | T | G | G | T | 3 |
| M1 | G | C | A | G | T | T | T | G | A | G | T | G | T | C | T | C | T | G | G | T | 3 |
| M10 | G | C | A | G | T | T | T | G | A | G | T | G | T | C | T | C | T | G | G | T | 3 |
| M2 | G | C | A | G | T | T | T | G | A | A | T | G | T | C | T | C | T | G | G | T | 4 |
| M3 | G | C | A | G | T | T | T | G | A | A | T | G | T | C | T | C | T | G | G | T | 4 |
| M4 | G | C | A | G | T | T | T | G | A | A | T | G | T | C | T | C | T | G | G | T | 4 |
| M5 | G | C | A | G | T | T | T | G | A | G | T | G | T | C | T | C | T | G | G | T | 3 |
| M6 | G | C | A | G | T | T | T | G | A | A | T | G | T | C | T | C | T | G | G | T | 4 |
| M7 | G | C | A | G | T | T | T | G | A | G | T | G | T | C | T | C | T | G | G | T | 3 |
| M8 | G | C | A | G | T | T | T | G | A | G | T | G | T | C | T | C | T | G | G | T | 3 |
| M9 | G | C | A | G | T | T | T | G | A | A | T | G | T | C | T | C | T | G | G | T | 4 |

TABLE 4

| | | | | | | | | | | | | | | | | | SEQ ID NO: |
|---|---|---|---|---|---|---|---|---|---|---|---|---|---|---|---|---|---|
| starting sequence | G | T | A | A | A | T | G | C | T | C | T | G | C | A | A | A | T | A | A | C | 5 |
| M1 | G | T | A | A | A | T | G | C | T | C | T | G | C | A | A | A | T | A | A | C | 5 |
| M10 | G | T | A | A | A | T | G | C | T | C | T | G | C | A | A | A | T | A | A | C | 5 |
| M2 | G | T | A | A | A | T | G | C | T | C | T | G | C | A | A | A | T | A | A | C | 5 |
| M3 | G | T | A | A | A | T | G | C | T | C | T | G | C | A | A | A | T | A | A | C | 5 |
| M4 | G | T | A | A | A | T | G | C | T | C | T | G | C | A | A | A | T | A | A | C | 5 |
| M5 | G | T | N | A | N | T | N | C | T | G | N | G | C | A | A | N | T | A | N | C | 6 |
| M6 | G | T | A | A | A | T | G | C | T | C | T | G | C | A | A | A | T | A | A | C | 5 |
| M7 | G | T | A | A | A | T | G | C | T | C | T | G | C | A | A | A | T | A | A | C | 5 |
| M8 | G | T | A | A | A | T | G | C | T | C | T | G | C | A | A | A | T | A | A | C | 5 |
| M9 | G | T | A | A | A | T | G | C | T | C | T | G | C | A | A | A | T | A | A | C | 5 |

TABLE 5

| | | | | | | | | | | | | | | | | | SEQ ID NO: |
|---|---|---|---|---|---|---|---|---|---|---|---|---|---|---|---|---|---|
| starting sequence | G | G | C | T | C | C | A | A | G | C | G | G | T | G | C | C | C | G | G | C | 7 |
| M1 | G | G | C | T | C | C | A | A | G | C | G | G | T | G | C | N | C | G | N | C | 8 |
| M10 | G | G | C | T | C | C | A | A | G | C | G | G | T | G | C | C | C | G | G | C | 7 |
| M2 | G | G | C | T | C | C | A | A | G | C | G | G | T | G | N | N | C | G | N | C | 9 |
| M3 | G | G | C | T | C | C | A | A | G | C | G | G | T | G | C | N | N | G | N | C | 10 |
| M4 | G | G | C | T | C | C | A | A | G | C | G | G | T | G | C | C | C | G | N | C | 11 |
| M5 | G | G | C | T | C | C | A | A | G | C | G | G | T | G | C | N | N | G | G | N | 12 |
| M6 | G | G | C | T | C | N | N | N | T | N | G | N | N | N | N | N | N | N | N | C | 13 |
| M7 | G | G | C | T | C | C | A | A | G | C | G | G | T | G | C | N | C | G | N | C | 8 |
| M8 | G | G | C | T | C | C | A | A | G | C | G | G | T | G | C | N | C | G | G | C | 14 |
| M9 | G | G | C | T | C | C | N | A | A | T | G | G | T | N | N | N | N | G | N | C | 15 |

TABLE 6

| | | | | | | | | | | | | | | | | | | SEQ ID NO: |
|---|---|---|---|---|---|---|---|---|---|---|---|---|---|---|---|---|---|---|
| starting sequence | G | A | C | C | T | C | T | T | T | A | G | C | T | C | G | T | T | A | T | T | 16 |
| M1  | G | A | C | C | T | C | T | T | T | G | C | T | C | G | T | T | A | T | T | 17 |
| M10 | G | A | C | C | T | C | T | T | T | A | G | C | T | C | G | T | T | A | T | T | 16 |
| M2  | G | A | C | C | T | C | T | T | T | A | G | C | T | C | G | T | T | A | T | T | 16 |
| M3  | G | A | C | C | T | C | T | T | T | A | G | C | T | C | G | T | T | A | T | T | 16 |
| M4  | G | A | C | C | T | C | T | T | T | A | G | C | T | C | G | T | T | A | T | T | 16 |
| M5  | G | A | C | C | T | C | T | T | T | A | G | C | T | C | G | T | T | A | T | T | 16 |
| M6  | G | A | C | C | T | C | T | T | T | A | G | C | T | C | G | T | T | A | T | T | 16 |
| M7  | G | A | C | C | T | C | T | T | T | A | G | C | T | C | G | T | T | A | T | T | 16 |
| M8  | G | A | C | C | T | C | T | T | T | A | G | C | T | C | G | T | T | A | T | T | 16 |
| M9  | G | A | C | C | T | C | T | T | T | A | G | C | T | C | G | T | T | A | T | T | 16 |

15

TABLE 7

| | | | | | | | | | | | | | | | | | | SEQ ID NO: |
|---|---|---|---|---|---|---|---|---|---|---|---|---|---|---|---|---|---|---|
| starting sequence | G | G | G | C | C | T | C | A | A | G | A | T | T | T | G | A | T | T | T | C | 18 |
| M1  | G | G | G | C | C | T | C | A | A | G | A | T | T | T | G | A | T | T | T | C | 18 |
| M10 | G | G | G | C | C | T | C | A | A | G | A | T | T | T | G | A | T | T | T | C | 18 |
| M2  | G | G | G | C | C | T | C | A | N | T | T | T | T | T | G | A | T | T | T | C | 19 |
| M3  | G | G | G | C | C | T | C | A | N | T | T | T | T | T | G | A | T | T | T | C | 19 |
| M4  | G | G | G | C | C | T | C | A | A | G | A | T | T | T | G | A | T | T | T | C | 18 |
| M5  | G | G | G | C | C | T | C | A | A | G | A | T | T | T | G | A | T | T | T | C | 18 |
| M6  | G | G | G | C | C | T | C | A | A | G | A | T | T | T | G | A | T | T | T | C | 18 |
| M7  | G | G | G | C | C | T | C | A | A | G | A | T | T | T | G | A | T | T | T | C | 18 |
| M8  | G | G | G | C | C | T | C | A | A | G | A | T | T | T | G | A | T | T | T | C | 18 |
| M9  | G | G | G | C | C | T | C | A | A | G | A | T | T | T | G | A | T | T | T | C | 18 |

TABLE 8

| | | | | | | | | | | | | | | | | | | SEQ ID NO: |
|---|---|---|---|---|---|---|---|---|---|---|---|---|---|---|---|---|---|---|
| starting sequence | A | G | G | G | G | G | C | T | T | T | T | C | C | A | G | C | T | C | 20 |
| M1  | A | G | G | G | G | G | C | T | C | T | T | T | C | C | A | G | C | T | C | 21 |
| M10 | A | G | G | G | G | G | G | C | T | T | T | T | C | C | A | G | C | T | C | 20 |
| M2  | A | G | G | G | G | G | C | T | C | T | T | T | C | C | A | G | C | T | C | 21 |
| M3  | A | G | G | G | G | G | C | T | C | T | T | T | C | C | A | G | C | T | C | 21 |
| M4  | A | G | G | G | G | G | C | T | C | T | T | T | C | C | A | G | C | T | C | 21 |
| M5  | A | G | G | G | G | G | C | T | C | T | T | T | C | C | A | G | C | T | C | 21 |
| M6  | A | G | G | G | G | G | C | T | C | T | T | T | C | C | A | G | C | T | C | 21 |
| M7  | A | G | G | G | G | G | C | T | C | T | T | T | C | C | A | G | C | T | C | 21 |
| M8  | A | G | G | G | G | G | C | T | C | T | T | T | C | C | A | G | C | T | C | 21 |
| M9  | A | G | G | G | G | G | C | T | C | T | T | T | C | C | A | G | C | T | C | 21 |

TABLE 9

| | | | | | | | | | | | | | | | | | | SEQ ID NO: |
|---|---|---|---|---|---|---|---|---|---|---|---|---|---|---|---|---|---|---|
| starting sequence | G | C | C | T | C | C | T | T | C | G | T | T | C | T | A | C | G | A | C | A | 22 |
| M1  | G | C | C | T | C | C | T | T | C | G | T | T | C | T | A | C | G | A | C | A | 22 |
| M10 | G | C | C | T | C | C | T | T | C | G | T | T | C | T | A | C | G | A | C | A | 22 |
| M2  | G | C | C | T | C | C | T | T | C | G | T | T | C | T | A | C | G | A | C | A | 22 |
| M3  | G | C | C | T | C | C | T | T | C | G | T | T | C | T | A | C | G | A | C | A | 22 |
| M4  | G | C | C | T | C | C | T | T | C | G | T | T | C | T | A | C | G | A | C | A | 22 |
| M5  | G | C | C | T | C | C | T | T | C | G | T | T | C | T | A | C | G | A | C | A | 22 |
| M6  | G | C | C | T | C | C | T | T | N | A | T | T | C | T | A | C | G | A | C | A | 23 |
| M7  | G | C | C | T | C | C | T | T | C | G | T | T | C | T | A | C | G | A | C | A | 22 |
| M8  | G | C | C | T | C | C | T | T | C | G | T | T | C | T | A | C | G | A | C | A | 22 |
| M9  | G | C | C | T | C | C | T | T | C | A | T | T | C | T | A | C | G | A | C | A | 24 |

TABLE 10

| | | | | | | | | | | | | | | | | | | | SEQ ID NO: |
|---|---|---|---|---|---|---|---|---|---|---|---|---|---|---|---|---|---|---|---|
| starting sequence | A | G | G | G | T | G | C | G | C | G | T | C | C | T | C | A | C | C | T | G | 25 |
| M1  | A | G | G | G | T | G | C | G | C | G | T | C | C | T | C | A | C | C | T | G | 25 |
| M10 | A | G | G | G | T | G | C | G | C | G | T | C | C | T | C | A | C | C | T | G | 25 |
| M2  | A | G | G | G | T | G | C | G | C | G | T | C | C | T | C | A | C | C | T | G | 25 |
| M3  | A | G | G | G | T | G | C | G | C | G | T | C | C | T | C | A | C | C | T | G | 25 |
| M4  | A | G | N | G | T | N | C | G | N | A | T | C | C | T | C | A | C | C | T | G | 26 |
| M5  | N | G | G | G | T | G | C | G | C | G | T | C | C | T | C | A | N | C | T | G | 27 |
| M6  | A | G | G | G | T | G | C | G | C | G | T | C | C | T | C | A | C | C | T | G | 25 |
| M7  | A | G | G | G | T | G | C | G | C | G | T | C | C | T | C | A | C | C | T | G | 25 |
| M8  | A | G | G | G | T | G | C | G | C | G | T | C | C | T | C | A | C | C | T | G | 25 |
| M9  | A | G | G | G | T | G | C | G | C | G | T | C | C | T | C | A | C | C | T | G | 25 |

TABLE 11

| | | | | | | | | | | | | | | | | | | SEQ ID NO: |
|---|---|---|---|---|---|---|---|---|---|---|---|---|---|---|---|---|---|---|---|
| starting sequence | A | A | C | C | A | G | A | A | T | T | T | A | T | T |   | T | G | A | G | G | 28 |
| M1  | A | A | C | C | A | G | A | A | T | T | T | A | T | T | T | T | G | A | G | G | 28 |
| M10 | A | A | C | C | A | G | A | A | T | T | T | A | T | T | T | T | G | A | G | G | 28 |
| M2  | A | A | C | C | A | G | A | A | T | T | T | A | T | T | T | T | G | A | G | G | 28 |
| M3  | A | A | C | C | A | G | A | A | T | T | T | A | T | T | T | T | G | A | G | G | 28 |
| M4  | A | A | C | C | A | G | A | A | T | G | T | A | T | T | T | T | G | A | G | G | 29 |
| M5  | A | A | C | C | A | G | A | A | T | T | T | A | T | T | T | T | G | A | G | G | 28 |
| M6  | A | A | C | C | A | G | A | A | T | T | T | A | T | T | T | T | G | A | G | G | 28 |
| M7  | A | A | C | C | A | G | A | A | T | T | T | A | T | T | T | T | G | A | G | G | 28 |
| M8  | A | A | C | C | A | G | A | A | T | T | T | A | T | T | T | T | G | A | G | G | 28 |
| M9  | A | A | C | C | A | G | A | A | T | T | T | A | T | T | T | T | G | A | G | G | 28 |

---

What is claimed is:

1. An isolated nucleic acid segment of between 10 and 100 bases of which at least 10 contiguous bases including a polymorphic site are from a sequence selected from the group consisting of SEQ ID NOS:1–5, SEQ ID No:5 in which the C at position 10 is replaced by a G, SEQ ID No:7, SEQ ID No:7 in which the C at position 10 is replaced by a T, SEQ ID Nos:16–18, SEQ ID No:18 in which the G at position 10 is replaced by a T, SEQ ID Nos:20–22, SEQ ID Nos:24 and 25, SEQ ID No:25 in which the G at position 10 is replaced by an A, SEQ ID Nos:28 and 29, and the perfect complements thereof, wherein the polymorphic site occurs at position 10 in each of the SEQ. ID Nos.

2. The isolated nucleic acid segment of claim 1 that is DNA.

3. The isolated nucleic acid segment of claim 1 that is RNA.

4. The isolated nucleic acid segment of claim 1 that is less than 50 bases.

5. The isolated nucleic acid segment of claim 1 that is less than 20 bases.

6. The isolated nucleic acid segment of claim 1, wherein the ten contiguous bases are from a sequence selected from the group consisting of SEQ ID Nos:2 and 4, SEQ. ID. No:5 in which the C at position 10 is replaced by a G, SEQ ID No:7 in which the C at position 10 is replaced by a T, SEQ ID. No:17, SEQ ID No:18 in which the G at position 10 is replaced by a T, SEQ ID Nos:21 and 24, SEQ ID NO:25 in which the G at position 10 is replaced by an A, SEQ ID No:29, and the perfect complements thereof, wherein the polymorphic site occurs at position 10 in each of the SEQ ID NOS.

7. The isolated nucleic acid segment of claim 1, which is a probe, and wherein the polymorphic site occupies a central position of the probe.

8. The nucleic acid of claim 1, which is a primer and, wherein the polymorphic site occupies the 3' end of the primer.

9. An isolated nucleic acid fragment of a human X chromosome comprising at least 10 contiguous bases including a polymorphic site from a sequence selected from the group consisting of SEQ ID Nos:2 and 4, SEQ ID No:5 in which the C at position 10 is replaced by a G, SEQ ID No:7 in which the C at position 10 is replaced by a T, SEQ ID No:17, SEQ. ID. No:18 in which the G at position 10 is replaced by a T, SEQ ID NOS:21 and 24, SEQ ID NO:25 in which the G at position 10 is replaced by an A, SEQ ID NO:29, and the perfect complements thereof, wherein the polymorphic site occurs at position 10 in each of the SEQ ID NOS.

10. The isolated nucleic acid fragment of a human X-chromosome of claim 9, comprising a sequence selected from the group consisting of SEQ ID NOS:2 and 4, SEQ ID NO:5 in which the C at position 10 is replaced by a G, SEQ ID NO:7 in which the C at position 10 is replaced by a T, SEQ ID NO: 17, SEQ. ID NO: 18 in which the G at position 10 is replaced by a T, SEQ ID NOS:21 and 24, SEQ ID NO: 25 in which the G at position 10 is replaced by an A, SEQ ID NO: 29, and the perfect complements thereof, wherein the polymorphic site occurs at position 10 in each of the SEQ. ID NOS.

11. A method of determining a base occupying a polymorphic site in a nucleic acid, comprising:

obtaining the nucleic acid from an individual; and determining a base occupying a polymorphic site in a sequence selected from the group consisting of SEQ ID NOS:2 and 4, SEQ ID NO:5 in which the C at position 10 is replaced by a G, SEQ ID NO:7 in which the C at position 10 is replaced by a T, SEQ ID NO:17, SEQ. ID NO:18 in which the G at position 10 is replaced by a T, SEQ ID NOS:21 and 24, SEQ ID NO:25 in which the G at position 10 is replaced by an A, SEQ ID NO:29, and the perfect complements thereof, wherein the polymorphic site occurs at position 10 in each of the SEQ ID NOS.

12. The method of claim 11, wherein the determining comprises determining a set of bases occupying a set of polymorphic sites in a set of sequences selected from the group consisting of SEQ ID NOS:2 and 4, SEQ ID NO:5 in which the C at position 10 is replaced by a G, SEQ ID NO:7 in which the C at position 10 is replaced by a T, SEQ ID NO: 17, SEQ. ID NO: 18 in which the G at position 10 is replaced by a T, SEQ ID NOS:21 and 24, SEQ ID NO:25 in which the G at position 10 is replaced by an A, SEQ ID NO:29, and the perfect complements thereof, wherein the polymorphic site occurs at position 10 in each of the SEQ. ID NOS.

13. The method of claim 12, wherein the nucleic acid is obtained from a plurality of individuals, and a base occupying one of the polymorphic sites is determined in each of the individuals, and the method further comprising testing each individual for the presence of a disease phenotype, and correlating the presence of the disease phenotype with the base.

* * * * *